United States Patent [19]
Godik

[11] Patent Number: 5,747,789
[45] Date of Patent: May 5, 1998

[54] METHOD FOR INVESTIGATION OF DISTRIBUTION OF PHYSIOLOGICAL COMPONENTS IN HUMAN BODY TISSUES AND APPARATUS FOR ITS REALIZATION

[75] Inventor: Eduard E. Godik, Midland Park, N.J.

[73] Assignee: Dynamics Imaging, Inc., Devon, Pa.

[21] Appl. No.: 678,786

[22] Filed: Jul. 11, 1996

Related U.S. Application Data

[63] Continuation of Ser. No. 160,396, Dec. 1, 1993, abandoned.

[51] Int. Cl.$^6$ .............................. A61B 5/00; G01N 21/00
[52] U.S. Cl. ................. 250/208.1; 250/226; 250/330; 250/339.02; 250/341.8; 128/633; 364/413.13
[58] Field of Search ................... 250/226, 208.1, 250/562, 330, 339.02, 363.02, 363.09, 341.8, 341.5, 341.1; 128/691, 664, 665, 654, 633, 653.1; 364/413.13

[56] References Cited

U.S. PATENT DOCUMENTS

| | | | |
|---|---|---|---|
| 3,878,392 | 4/1975 | Yew et al. | 250/306 |
| 3,897,150 | 7/1975 | Bridges et al. | 356/5 |
| 4,212,306 | 7/1980 | Mahumud | 128/665 |
| 4,281,645 | 8/1981 | Jöbsis | 128/633 |
| 4,286,602 | 9/1981 | Guy | 128/665 |
| 4,312,357 | 1/1982 | Andersson et al. | 128/664 |
| 4,385,634 | 5/1983 | Bowen | 128/653 |
| 4,495,949 | 1/1985 | Stoller | 128/664 |
| 4,515,165 | 5/1985 | Carroll | 128/664 |
| 4,536,790 | 8/1985 | Kruger et al. | 128/691 |
| 4,570,638 | 2/1986 | Stoddart et al. | 128/665 |
| 4,576,173 | 3/1986 | Parker et al. | 128/633 |
| 4,583,869 | 4/1986 | Chive et al. | 374/122 |

(List continued on next page.)

FOREIGN PATENT DOCUMENTS

| | | |
|---|---|---|
| 0447708A3 | 9/1991 | European Pat. Off. |
| WO79/00594 | 8/1979 | WIPO |

OTHER PUBLICATIONS

Godik, E.E., Guljaev, Yu.V., "The Human Being Through 'Eyes of Radiophysics'", *Journal of Radio Engineering* (Russian) 1991, No. 8, pp. 51–56. (No Month).

Ring, E.F.J. and Hughes, H. "Real Time Video Thermography", in *Recent Developments in Medical and Physiological Imaging* a supplement to *Journal of Medical Engineering and Technology*, 1986, pp. 86–89. (No Month).

(List continued on next page.)

*Primary Examiner*—Edward P. Westin
*Assistant Examiner*—John R. Lee
*Attorney, Agent, or Firm*—Jacob N. Erlich; Jerry Cohen

[57] ABSTRACT

The method of investigation of physiological components distribution in human body tissues includes optical illumination of the investigated area, recording of the spatial distribution of the intensity of the light reflected by the investigated area within a definite period of time through sequential time intervals, which are small compared to the time constant of the investigated process. The wavelength of the illuminating or recorded reflected radiation is chosen at one of the spectral intervals with a maximal steepness of the spectral changes in the physiological pigments absorption, this radiation being modulated by the frequency and the amplitude-modulated part of the reflected light thus appearing is recorded synchronously at the modulation frequency. In one aspect of the method, the investigated area is illuminated at one or several points and the reflected radiation is recorded at points shifted relative to the illuminated ones. An apparatus for investigation of distribution of physiological components in human body tissues contains an illuminator for the optical illumination of the investigated area with a control block, a detecting device for recording of the investigated area images, means for assignment of the radiation wavelength, a system of image formation, a video control device, a dynamic interface board for formation and accumulation at the video memory of the image processing system of the frame sequence.

12 Claims, 4 Drawing Sheets

U.S. PATENT DOCUMENTS

| | | | |
|---|---|---|---|
| 4,616,657 | 10/1986 | Stoller | 128/664 |
| 4,649,275 | 3/1987 | Nelson et al. | 250/358.1 |
| 4,767,928 | 8/1988 | Nelson et al. | 250/341 |
| 4,798,209 | 1/1989 | Klingenbeck et al. | 128/653 |
| 4,810,875 | 3/1989 | Wyatt | 250/227 |
| 4,817,038 | 3/1989 | Knoll et al. | 250/363.02 |
| 4,817,622 | 4/1989 | Pennypacker et al. | 250/330 |
| 4,821,117 | 4/1989 | Sekiguchi | 358/98 |
| 4,829,184 | 5/1989 | Nelson et al. | 250/358.1 |
| 4,862,894 | 9/1989 | Fujii | 128/691 |
| 4,927,244 | 5/1990 | Bahr et al. | 350/350 S |
| 4,945,239 | 7/1990 | Wist et al. | 250/358.1 |
| 4,948,974 | 8/1990 | Nelson et al. | 250/358.1 |
| 4,955,383 | 9/1990 | Faupel | 128/653 R |
| 4,995,398 | 2/1991 | Turnidge | 128/668 |
| 5,079,698 | 1/1992 | Grenier et al. | 364/413.13 |
| 5,099,848 | 3/1992 | Parker et al. | 128/661.07 |
| 5,139,025 | 8/1992 | Lewis et al. | 128/665 |
| 5,170,119 | 12/1992 | Sekihara et al. | 324/260 |
| 5,197,470 | 3/1993 | Helfer et al. | 128/634 |
| 5,213,105 | 5/1993 | Gratton et al. | 128/664 |
| 5,222,495 | 6/1993 | Clarke et al. | 128/633 |
| 5,269,325 | 12/1993 | Robinson et al. | 128/653.1 |
| 5,293,873 | 3/1994 | Fang | 128/664 |
| 5,301,681 | 4/1994 | DeBan et al. | 128/736 |
| 5,303,026 | 4/1994 | Strobl et al. | 356/318 |
| 5,305,748 | 4/1994 | Wilk | 128/653.1 |
| 5,307,807 | 5/1994 | Sosa et al. | 128/653.1 |
| 5,309,907 | 5/1994 | Fang et al. | 128/633 |
| 5,311,018 | 5/1994 | Zana et al. | 250/330 |
| 5,313,941 | 5/1994 | Braig et al. | 128/633 |
| 5,333,610 | 8/1994 | Hirao | 128/633 |
| 5,337,745 | 8/1994 | Benaron | 128/633 |
| 5,361,758 | 11/1994 | Hall et al. | 128/633 |
| 5,363,854 | 11/1994 | Martens et al. | 128/665 |
| 5,371,368 | 12/1994 | Alfano et al. | 250/341.1 |
| 5,408,996 | 4/1995 | Salb | 128/633 |
| 5,445,157 | 8/1995 | Adachi et al. | 128/664 |
| 5,452,723 | 9/1995 | Wu et al. | 128/664 |
| 5,515,847 | 5/1996 | Braig et al. | 128/633 |
| 5,572,996 | 11/1996 | Doiron et al. | 128/633 |

OTHER PUBLICATIONS

Platonov, S.A., . . . , Godik, E.E., "Informative Tasks of Functional Mapping of Biological Subjects", *Journal of Radio Engineering* (Russian) 1991, No. 8, pp. 62–68. (No Month).

Jacquez, J.A. et al, "Spectral Reflectance of Human Skin in the Region 235–1000 nm", *Journal of Applied Physiology*, 1955, vol. 7, No. 3, pp. 523–528. (No Month).

"Physics of Image Visualization in Medicine", C. Webb, ed. vol. 2, pp. 241–243. (No Month).

Krenkel, T.E., Kogan, A.G. and Tatatorian, A.M., "Personal Computers in Engineering", Izd. Mir, RiS, (Russian) 1989, p. 71.—(No Month).

Dgagupov, R.G. and Erofeev, A.A., *Piezo–Ceramic Elements in Instrument Designing and Automatics*, Leningrad, Izd. Mashinosroenie, 1986, pp. 154–155 (Russian).

Legett, Kate*, *Optical mamography offers promise as alternative to x–ray detection*, Biophotonics International, Jan./Feb., 1996, pp. 56–57.

U.S. application No. 08/411,644, filed Aug. 14, 1995, now U.S. Pat. No. 5,699,797 issued on Dec. 23, 1997.

Godik, Eduard E. and Gulyaev, Uri, V., "Functional Imaging of the Human Body," *IEEE Engineering in Medicine and Biology*, Dec. 1991, pp. 21–29.

METHOD FOR INVESTIGATION OF DISTRIBUTION OF PHYSIOLOGICAL COMPONENTS IN HUMAN BODY TISSUES AND APPARATUS FOR ITS REALIZATION

CROSS REFERENCES TO RELATED APPLICATIONS

This application is a continuation of Ser. No. 08/160,396 filed Dec. 1, 1993 now abandoned.

FIELD OF THE INVENTION

The invention relates to the field of biomedical engineering, in particular, to optical methods and equipment for non-invasive investigation of blood content and distribution in human body tissues, it could be used for early diagnostics of pathologies connected, in particular, with functional disturbances in the blood supply of the skin and underlying tissues.

BACKGROUND OF THE INVENTION

Special attention devoted to optical methods and equipment for non-invasive biomedical investigations is challenged, primarily, by the absolute harmless and relative simplicity of the equipment employed (Physics of Image Visualization in Medicine, S. Webb, ed., 1991, volume 2, pp. 277–288, Mir, M.). It is the latter points that give the possibility to expect an important breakthrough to be achieved in the population screening, as well as in probing the functional and morphological status of living organism vital activity.

Different optical methods are known involving both passive and active means of the organism's optical investigation. In the first case, the organism's own radiation at the infrared (IR) range is recorded, while in the second case, external illumination of insignificant density, absolutely harmless for the human organism, is employed.

A method and apparatus for investigation of physiological components in human body tissues was described in Guljaev Yu. V., Godik E. E. et al. "On the possibilities of distance functional diagnostics of biological subjects via their own IR- radiation," USSR Academy of Science Reports 1984, vol. 277, p.1486–1489. According to this method, temporal changes in spatial distribution of IR thermal radiation of living organism tissues are recorded, reflecting in the form of thermal images spatial-temporal dynamics of the blood microcirculation near the surface layer of the area investigated. The apparatus for realization of this method contains an IR-thermovisor, a dynamic interface board for accumulation of the temporal sequences of thermal images and a computer system for the image processing.

However, the method and apparatus described in Guljaev Yu. V., Godik E. E. et al. Ibid., being rather complex for realization and operation, are restricted to the investigation of the capillary blood flow only at the most upper skin layers, since the characteristic depth of absorption of IR thermal radiation by the skin does not exceed 100μ.

The nearest to the method claimed from the known ones is a method of functional optical mapping (USSR Patent No 1375243, cl. A61B 5/00, 1985), including uniform illumination of the investigated area of a human body and recording this area images in the reflected light of a definite spectral range, blood distribution in the investigated area being judged by the images obtained. The apparatus for realization of a similar method is described in Stoller (U.S. Pat. No. 4,616,657, cl. A 61 B 6/12, 1986), containing a light source for optical illumination of the investigated area of a human body, a detector of the investigated area images, a video control device and special filters to provide the necessary illumination wavelength interval, the input of the system of the images formation is connected with the output of the detector, and the output—to the video control device.

The main disadvantage of the above mentioned method and apparatus is that they are capable of analyzing only a static picture of blood distribution and do not permit either visualization of the functional dynamics of the arteriovenous blood redistribution at the area investigated, nor the estimation of the content and the temporal changes of physiological liquids in tissues which are characterized by specific optical absorption features.

SUMMARY OF THE INVENTION

The present invention obtains the most complete information on the functional state of the human body physiological systems with the help of recording spatial-temporal distributions of radiation intensity reflected by an investigated area of a human body at definite spectral ranges.

This task is solved by a modification of the known methods of investigation of physiological components in human body, involving optical illumination of the investigated area and recording of spatial distribution of the intensity of light reflected by the investigated area at certain spectral intervals, which is distinguished by recording of frames of spatial distributions of the reflected light intensity performed at fixed time moments through time intervals small enough as compared with the time constant of the process investigated. To increase the method sensitivity to the concentration of physiological pigments of interest (of blood hemoglobin, first of all), at the background of only slightly wavelength dependent light reflection from the investigated surface and of back scattering from the epidermis, not containing blood vessels, the wavelengths of the illuminating radiation or/and of the recorded reflected one are chosen at one of the spectral intervals with the maximal steepness in the absorption spectral changes of the physiological pigments. This radiation is modulated by frequency with a period of the modulation much less than the frame recording time. Under these conditions the amplitude-modulated part of the reflected radiation is synchronously recorded at the modulation frequency. The investigated area can be illuminated at one or several points distributed over it, with the reflected radiation being recorded at points shifted relative to the illuminated ones. To obtain a continuous imaging with maximal probing depth and sensitivity, a scanning of the investigated area by the illuminating points is performed, the scanning velocity securing one frame recording time being much less than the time constant of variability in the intensity of light reflected by the investigated area.

The invention task is achieved also by inclusion into the known apparatus for investigation of physiological components distribution in human body tissues, an illuminator with a control block for optical illumination of the investigated area of human body, a detector for image recording of the investigated area, optical filters to provide the necessary illumination wavelength, a system of image formation and a video control device, an additional dynamic interface board for formation and accumulation, at a video memory of the image processing system, of the sequence of frames, the board input being connected with the output of the image formation system output, and the output—with the video control device. The apparatus can contain a modulator for the illuminating and/or received radiation frequency and a synchronous accumulator of the spectral image differences for different radiation frequencies within the range of the modulation band, the modulator input being connected with the detector device output, and the output—with the dynamic interface board. The illuminator could be an array of light illuminators, the distance between the latter being much larger than their size and that of the optical system for projecting the light sources images to the investigated area, each of the light sources being coupled to the control block output. The optical system for projecting the light sources images to the investigated area could contain special means for variation of the size, form and the position of light sources' images at the surface of the area investigated. The detector device for the image recording can be in the form of an array of photodetectors, each of the latter being coupled to the synchronous detector, connected with the image formation system input, and to the optical system for projecting the image of the investigated area to this array; each of the array photodetectors can consist of at least two sensitive elements adjusted for measurements at different spectral ranges. The apparatus can contain both an array, an image detector and a detection television camera together with a system of electric image superposition and a system of optical correction of this superposition. The illuminator can be an array of light sources, each containing at least two illuminators with different spectral position of the radiation maxima, the distance between the illuminators being much less than the array step; the sum of full widths at half maxima (FWHM) of the radiation bands for each illuminator must be less than the wavelength difference of these absorption bands maxima. The illuminator and the detection device could be a single array, the illumination sources and the photodetectors being placed in a chess board fashion or in the form of alternating lines.

DETAILED DESCRIPTION OF THE PREFERRED EMBODIMENTS

Figures 1A, 1B:
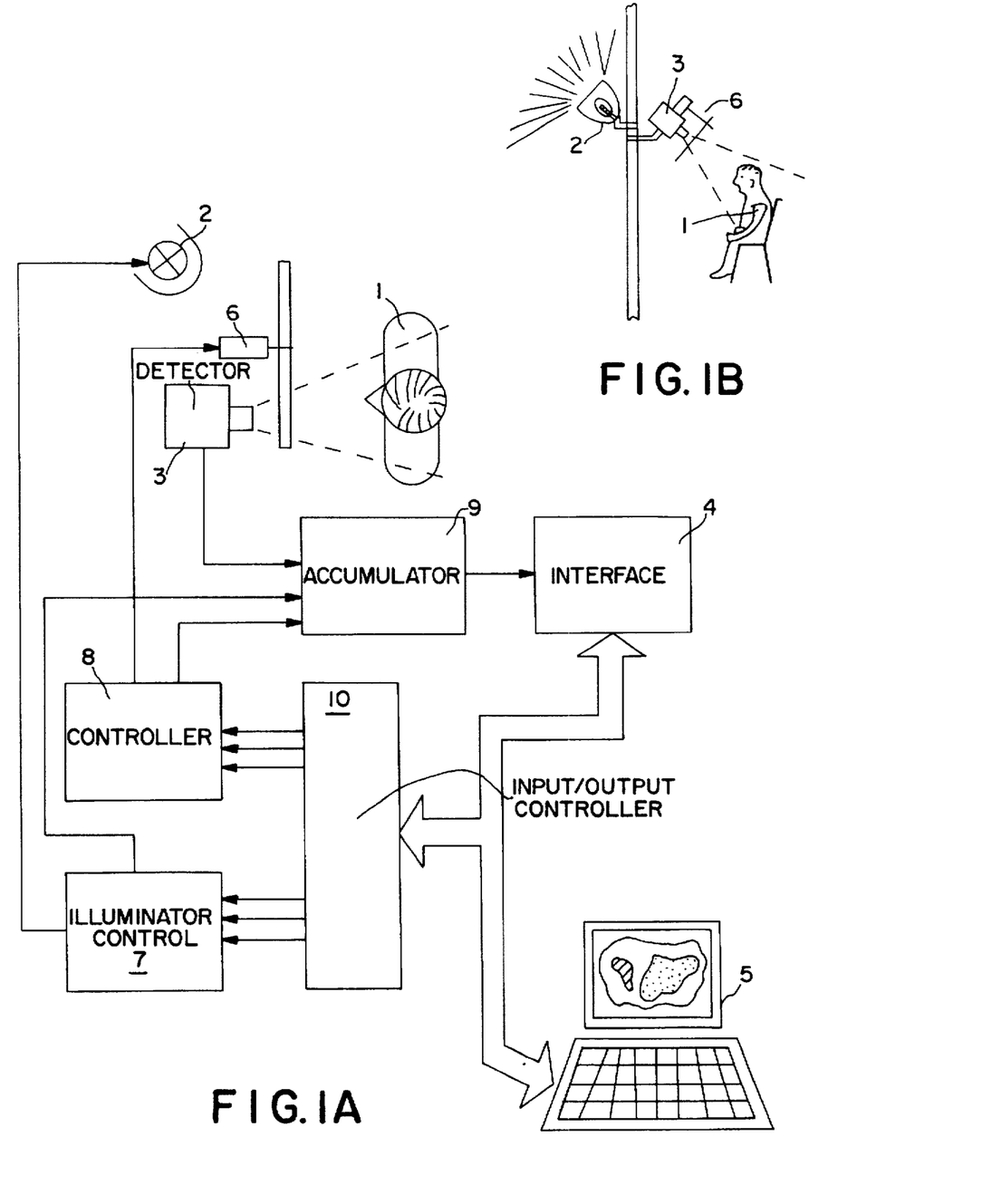
FIG. 1A shows in schematic fashion an embodiment of the apparatus where the investigated area shown in FIG. 1B is uniformly illuminated and the distribution of the intensity of the scattered light is recorded with the help of a television camera.
FIG. 1B is a pictorial representation of the investigated area.

The claimed method of the investigation of the physiological components in human body tissues is based on the dependence of the intensity of light, scattered by the investigated surface, on the physiological liquids content at the near surface tissue layers. The distribution of the scattered light intensity over the investigated subject surface represents, to the point, its image at the given wavelength. The method can be realized with the help of an apparatus shown in FIG. 1, where 1 is an investigated area of a human body, 2 is an illuminator, 3 is a detecting device, 4 is a dynamic interface board, 5 is a computer with a video control device, 6 is a device for the frequency modulation of the recorded radiation supplied with a driver; 7 is an illuminator control block, 8 is a control block of the detecting spectral band, 9 is a synchronous accumulator of the spectral images differences and 10 is an input output controller.

To realize the suggested method, the investigated area 1 of human body is illuminated by optical radiation with the help of illuminator 2, consisting of a diffusely scattering reflector, with the size much larger than that of the investigated area, and of at least one light source, turned to the reflector, which is put up so that to avoid a direct light falling into the investigated area, and manageable block 7 of the illuminator control. The spatial distribution of the intensity of light reflected from the investigated area is recorded at fixed time moments through sequential time intervals, small enough as compared with the time constant of the process investigated, with the help of detecting device 3 supplied with a system of formed images, of synchronous accumulator 9 of differences of spectral images and of dynamic interface board 4, coupled to computer 5 with video control device. The map sequences of the spatial distribution of the intensity of the reflected light thus obtained gives information on a spatial picture of the functional dynamics of the arterial and venous capillary blood content. The illuminating radiation spectrum is assigned by a corresponding command from computer 5 via the illuminator control block 7 by means of changing spectral filters or by electric switching over the illuminator sources with different radiation spectra, photodiodes, for example. Spectrum of the recorded radiation could be put up by control block 8 of the detecting spectral band assignment.

To exclude the dependence of the results obtained on the spatial inhomogeneity of the illumination, the spatial distribution of the relative temporal changes in the intensity of the reflected radiation dI/I is determined. The latter parameter does not depend on the intensity of illuminating radiation. The temporal variability of dI/I at different spectral intervals is connected with the functional temporal dynamics of physiological pigments in biological tissues, of hemoglobin, in particular. By this reason, the dynamic mapping of dI/I that makes it possible to separate the contribution of the more deep tissue layers, containing blood capillaries, at the background of light reflected by the near surface layer of epidermis, as well as at the background of Fresnel's reflection. When a uniform, isotropic and stable in time illumination is used, relative changes in the reflective capability dR/R=dI/I are determined simply by the value of dI (I=constant). To create such an illumination, illuminator 2 is used with the dimensions of the illuminating surface much larger than that of the subject under the investigation (see FIG. 1).

To exclude the influence of the background illumination and the necessity, of using darken rooms for carrying out the measurements, brought about by the existence of such illumination, an amplitude modulation of the illuminating radiation is used with a synchronous detection at the modulation frequency. The modulation frequency of the illuminating radiation intensity is chosen to be much larger than that of the natural biological rhythms, including cardiopulsations. The relative non-stability in the amplitude of the radiation intensity modulation must be less than the relative changes in the reflective capability of the investigated area.

To separate the partial image dynamics, connected with changes in the microcirculation and cell metabolism, filtering of the illuminating and recorded radiation is carried out at the spectral ranges of the light absorption by the main physiological pigments of the biological tissues: oxyhemoglobin, deoxygenated hemoglobin and cytochrome aa3, for example. In addition, spectral selection of the radiation at the above mentioned ranges promotes the exclusion of only slightly wavelength dependent reflection of the illuminating radiation, coming from the near surface epidermis layer, not-containing blood vessels.

For performing an additional selection of signals connected with the tissue blood content at the background of epidermis, a frequency modulation of the illuminating radiation is performed at the wavelength ranges of a strong spectral dependence of the physiological pigments absorption, since optical absorption of epidermis is only slightly dependent on the radiation wavelength. The frequency modulation of the illuminating radiation results in an amplitude modulation of radiation reflected from the tissues, containing the physiological pigments, such radiation is recorded by synchronous detecting at the modulation frequency of the illuminating radiation wavelength. Under the conditions of such frequency modulation, the spectral band of the radiation used must be less than the frequency (wavelength) interval, over which the frequency (wavelength) modulation is performed. Taking into consideration spectral dependency of the reflective capability ($R=I/Io$) of biological tissues cited, for example, in Jacquez J. A. et al. Spectral Reflectance of Human Skin in the Region 235–1000 nm, J. Applied Physiology, 1955, vol. 7, No. 3, pp. 523–528, several spectral ranges could be separated, where abrupt changes in the absorption coefficient, as well as in the coefficients of the back scattering and reflective capability, take place. At the spectral range under investigation, the reflective capability is determined only in a small extent by Fresnel's reflection ($R_{suf}=4-6\%$) from the surface, and the main contribution is made by the radiation, back scattered from the tissues depth ($R_{scat}>50\%$), where the main physiological pigment, hemoglobin, and water are located. To record the total hemoglobin (oxy- and deoxy-) content in tissues of up to 2–3 mm depth, the radiation frequency (wavelength) is modulated at the spectral range of about $0.59\mu$ wavelength, the minimal wavelength is chosen to be in the wavelength interval from 0.53 to $0.58\mu$ (the main visible hemoglobin absorption band) and the maximal one— from 0.60 to $0.63\mu$. For recording hemoglobin content at a lesser depth (less than 1 mm), the wavelength near $0.43\mu$ is modulated, the minimal wavelength being chosen at the interval $0.38-0.43\mu$ (Sore band of hemoglobin absorption) and the maximal one at the range of $0.46-0.50\mu$.

To record the partial deoxygenated hemoglobin concentration, the wavelength modulation is performed near $0.68\mu$ wavelength, at which oxyhemoglobin absorption is minimal (frequency derivative is equal to zero). The modulation interval is chosen from 0.63 to $0.72\mu$.

Oxyhemoglobin absorption is dominant at $1.03-1.10\mu$ wavelength interval. As the reference interval while performing the frequency modulation, $0.8-0.9\mu$ wavelength interval is used, where hemoglobin absorption is minimal and practically independent of the degree of hemoglobin oxygenation, while the tissue reflective capability is maximal (Jacquez J. A. et al. Ibid.)

To record water concentration at the near surface tissues of up to 2–3 mm depth, the wavelength near $1.15\mu$ is modulated at $1.1-1.2\mu$ interval.

To record water concentration at less deep layer (about 1 mm), practically at epidermis, the wavelength modulation is performed near $1.35\mu$ wavelength at $1.3-1.4\mu$ wavelength interval.

Water content at still more shallow layer (horned epidermis layer) can be estimated via absorption at spectral window of $1.6-1.8\mu$; for performing the wavelength modulation under these conditions, as the reference wavelength, the wavelengths of $1.4\mu$ and $1.9-2.0\mu$ are used, at which the reflective capability is minimal and is determined practically by Fresnel's reflection from the surface.

Of special interest is the possibility of hematocrit estimation as the ratio of hemoglobin and water concentrations at the near surface tissues via comparison of the results of hemoglobin concentration measurements at $0.53-0.63\mu$ spectral interval with those of water at $1.1-1.2\mu$ wavelength interval, since at the above spectral intervals the reflective capability is formed at the expense of the back scattering by the tissues of practically identical thickness (the geometry of the diffusive light scattering for these wavelength intervals is similar). A similar possibility of hematocrit estimation emerges when the results of estimation of hemoglobin concentration obtained at $0.38-0.50\mu$ wavelength interval of hemoglobin absorption and those obtained at $1.3-1.4\mu$ interval of water absorption are compared.

Instead of modulation of the illuminating radiation wavelength, a wide band illumination with the spectral band wider than the modulation intervals can be used; in this case, the detecting spectral band of the photodetectors is modulated with a subsequent synchronous detecting of an appearing amplitude-modulated signal.

The application of such a frequency modulation makes it possible to decrease a parasite influence of the illumination instabilities (flicker-effects), including those provoked by the subject movements, since appearing under these conditions amplitude modulated signal is formed during the frequency modulation period, the latter is chosen to be much less than the characteristic instability time.

In order to modulate the frequency of the illuminating or recorded radiation, either periodic change of spectral filters is performed, or periodic switching of the illuminating or/and recording elements with variable spectrum of illumination or detection is employed. Under these conditions, the intensities of the illuminating radiation are carefully equalized in the limits of the spectral band of the modulation. When detection is performed with the help of a television camera based on a CCD-array, for example, the image of the investigated subject, obtained at one of the frequencies from the modulation band synchronously with the filter changing, is counted with the help of an array control block and stored at the buffer memory (of other CCD array, for example). The other image, obtained synchronously with changing the filters to provide another frequency, is subtracted from the first one. The image difference thus obtained is accumulated either at the same buffer memory or at an additional one during a time interval much less than the time constant of the process investigated (usually the accumulation time is chosen to be 0.1–10 s). The synchronous accumulation of the spectral image differences may be also performed in a digital form by digitizing each frame and using a digital-video memory with a microprocessor, for example, DT-2861 board of DATA TRANSLATION. Thus accumulated differences of the spectral images are sent with the help of a dynamic interface board to a video memory of a personal computer for further data processing. Instead of the spectral filters, two-color (or multi-color) CCD camera can be used accumulating differences of the spectral images.

When the area investigated is illuminated with uniform homogeneous radiation, the main contribution to the recorded reflected signal is made by back scattered radiations coming from the depth of 2-3 mm. Under these conditions, together with a restricted probing depth, the sensitivity to the pigment concentration is also restricted, since the degree of the intensity of the back scattered radiation weakening is determined by the product of the pigment absorption coefficient (K) and the radiation path length (l) at the investigated tissue. Some increase in the probing depth and the sensitivity can be achieved via separation with the help of the spectral filters of the wavelength range>0.8µ, where oxyhemoglobin absorption dominates due to a deeper location of the arterial layer as compared with the near surface venous network.

For a considerable increase in the sensitivity and probing depth, inhomogenous illumination of the investigated area at one or several points is used. When the radiation recording is performed at the points (or at circular areas) shifted relative to the illumination point by a sufficient distance (radius r), then the sensitivity is increased proportionally to r, under the condition that r>>1/K.

where:

$$\chi = \sqrt{3/(l_{scat} * l_{abs})}$$

$l_{abs} = (G_n * N_n^{-1})$, $l_{scat} = (G_n * N_p^{-1})$ are the absorption and scattering depths, $G_n$ and $G_p$ are the absorption and scattering cross-sections;

$N_p$ and $N_n$ are the concentrations of the scattering and absorption centers. Usually in biological tissues, 1/K=3-5 mm.

Under these conditions, the relative change in the reflective capability, at the radiation frequency modulation, is given by the following relation:

$$\Delta R/R = (r/2) * K^{1/2} * (\Delta G/G),$$

and when the concentration of the physiological pigment N is changed, then $$R/R = (r/2) * K^{1/2} * (\Delta N/N)$$

The probing depth increases under these conditions approximately as $\sqrt{r}$.

Figure 2:
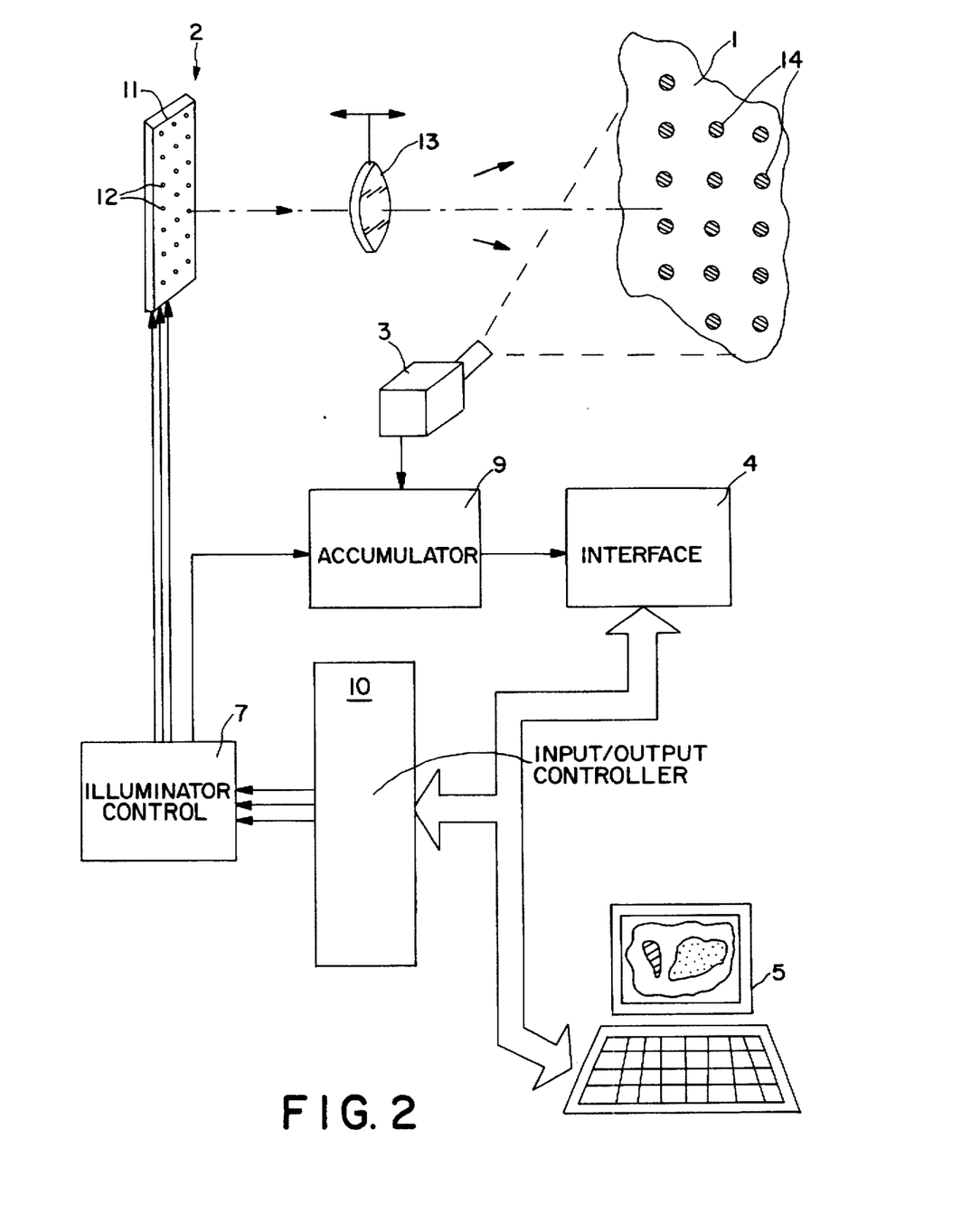
FIG. 2 shows in a schematic representation of another embodiment of the apparatus employing an illumination source in the form of an array of light sources.

For realization of the inhomogenous illumination, another embodiment of the apparatus is shown in FIG. 2. It contains illuminator 2, in the form of an array 11 of light sources 12 and coupled with the output of the illuminator control block 7, and an optical system 13 for projecting of the images of the light sources 12 to the living organism investigated area 1. The distance between light sources 12 being much larger than their size. The points illuminated are marked out in FIG. 2 by position 14.

To perform optimal distribution of the illuminated points over the investigated area, optical system 13 for projecting of light sources 12 images is supplied with special means for variation of the size, form and the position of the light sources images at the surface of the investigated area (not shown in FIG. 2). Such means are well known in engineering, zoom-transfocators, cylindrical lens etc. belong to them. The apparatus, shown in FIG. 2, is capable of functioning at the mode of the amplitude and frequency modulation of the illuminating radiation with the corresponding demodulation of the recorded radiation, in accordance with the synchronous detecting principle. The amplitude modulation in this apparatus is realized via light sources 12 current modulating, the detection device 3 being coupled to dynamic interface 4 through synchronous accumulator 9 of the spectral images differences. As the reference signals for synchronous accumulator 9, the synchronizing signals from block 7 of the illuminator control are utilized.

Figure 3:
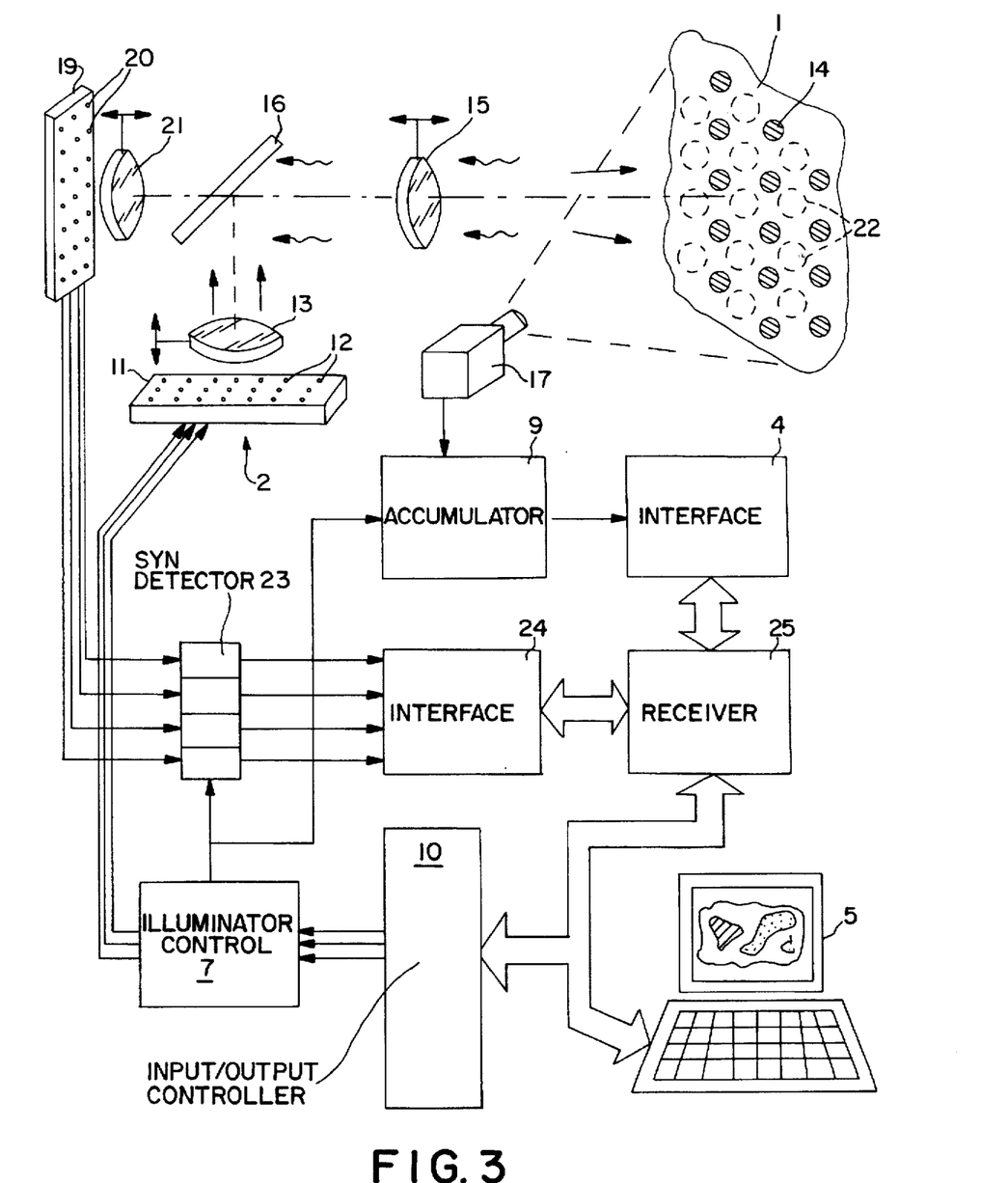
FIG. 3 is a portion of the apparatus containing an array illuminator and, in addition to a television camera, an array detection device with a synchronous detector at each photodetector chain.

In order to record radiation, reflected from or back scattered by investigated area 1, at points, shifted relative to the illuminated points 14, another embodiment of the apparatus is shown in FIG. 3. In this device, the investigated area 1 is illuminated with the help of illuminator 2, fulfilled as array 11 of light sources 12, and an optical device containing optical systems 13 and 15 and semitransparent mirror 16. The optical systems project the images of the light sources 12 to investigated area 1.

The illumination regime- brightness, the frequency of illuminating radiation—is managed by block 7 of the illuminator control, coupled via input-output controller 10 with computer 5.

The image of the investigated area (i.e. spatial distribution of the reflected light intensity) in the form of the temporal frame sequence is recorded with the help of a detection device—video camera 17, coupled with synchronous accumulator 9 of the spectral images differences and further with dynamic interface board 4 of the video camera; another detection device is also used consisting of array 19 of photodetectors 20 and optical system 21 of the investigated area 1 image projecting to this array.

In the simplest case, array 19 of photodetectors 20 is similar to array 11 of light sources 12. Displacement of array 19 of photodetectors relative to optical systems 15 and 21 makes it possible to record the reflected radiation at points 22, which are shifted relative to the illuminated points 14 at the surface of the investigated area. Photodetectors 20 are coupled to synchronous detectors 23, the outputs of the latter being connected with dynamic interface board 4 and 24 of the photodetectors array.

The signals from dynamic interface boards 18 and 24 of video camera 17 and photodetectors array 19 are received, via system 25 of the image superposition, by computer 5 with a video control device. The image superposition permits combination of high sensitivity and probing depth, achieved with the photodetector array, and fine spatial representation of the investigated area, given by the camera.

Figure 4:
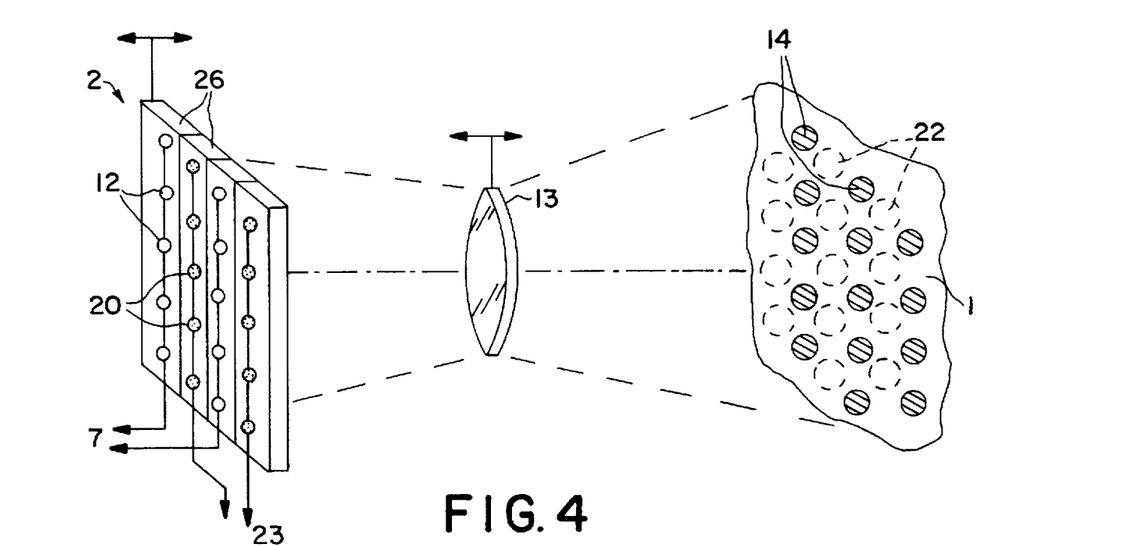
FIG. 4 shows a portion of the apparatus where the illuminator and photodetector arrays are united into a single array, the illuminators and photodetectors being in alternate lines.

The illuminator and the detection device can be in the form of a single array (see FIG. 4) with light sources 12 and photodetectors 20 located alternatively in a chess board fashion; in this case, the distance between the neighboring sources must exceed considerably their size. Such mode of the illuminator and the photodetection device realization makes it possible to simplify considerably the construction of optical system 13. From a technological point of view, the light source arrays and the photodetectors are in the form of alternating illuminators and photodetectors lines 26.

Figure 5:
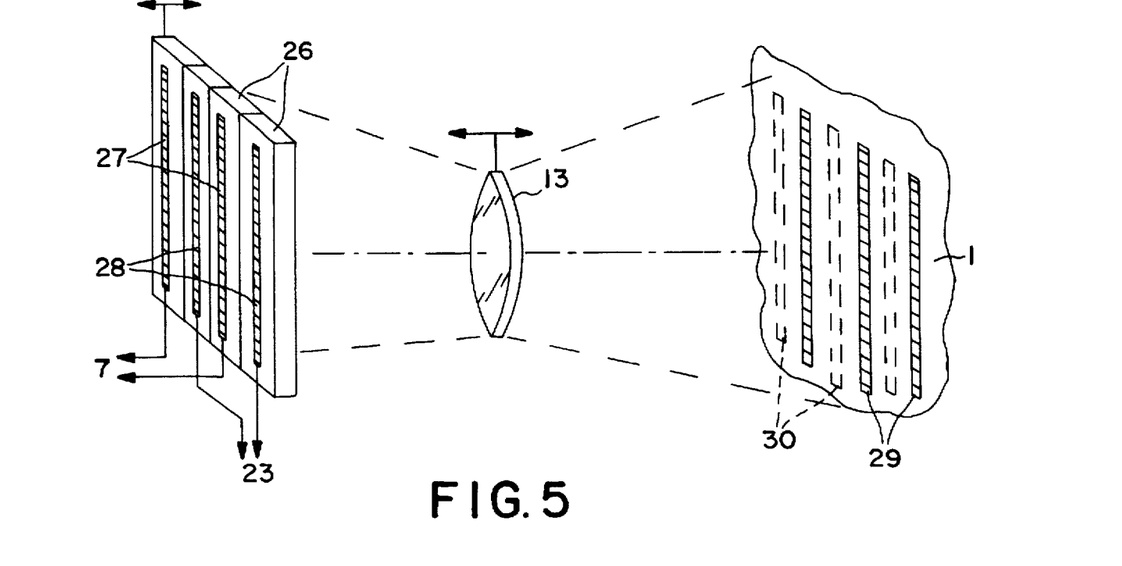
FIG. 5 is similar to that shown in FIG. 4 with the illuminators and the photodetectors are performed alternating bands.

Another manner of integrating the illuminator and the photodetection device is in the form of a single array formed of alternating band illuminators 27 and band photodetectors 28 (see FIG. 5). In this case, the illuminated parts 29 at the surface of the investigated area 1 and parts 30, at which the reflected radiation is recorded, represent alternating bands.

Thus, the apparatus claimed permit carrying out the measurements via several different modes.

The frequency modulation of the illuminating radiation can be realized, for example, by means of a fast change of narrow band optical filters, placed in front of a wide band optical radiation source, an incandescent lamp, for example. If the illuminator is the light source array, then frequency modulation is possible using the light sources consisting of two illuminators with different spectral maxima of radiation, located at a mutual distance much less than the array step and connected with the control block, and switching over these illuminators by the latter block alternatively with the modulation frequency. To increase the sensitivity of such measurements, the sum of FWHM of the radiation bands is necessary to be chosen less than difference in the wavelengths of these bands maxima.

Instead of modulation of the illuminating radiation frequency, wide band illumination can be applied with the spectrum band larger than the modulation interval, and to modulate the detecting spectral band of the photodetectors with subsequent synchronous detecting of the amplitude modulated signal appearing.

With this purpose, a fast change of narrow band spectral filters, located before detection device 3, is realized with the help of block 8 of the detecting spectral band control and device 6 of the frequency modulation of the received radiation (see FIG. 1). In the case, when the detecting device is in the form of the photodetector arrays, modulation of the recorded radiation frequency is carried out by means of each of the arrays of photodetectors being in the form of two sensitive elements with different spectral sensitivity, coupled to the control block, and switching over these elements with the help of the latter block with the frequency of the modulation. The distance between these elements must be much less than the array step. Sufficient sensitivity of measurements can be achieved under these conditions, if the sum of FWHM of the detectors spectral sensitivity bands is less than the difference in the wavelengths of these bands maxima.

It should be mentioned that the realization of the apparatus can be performed with the help of known technical systems. Thus, as the dynamic interface boards (4, 18 and 20), known video microprocessors for computers, performing images input and visualization (Krenkel T. E. et al. *Personal Computers in the Engineering Practices*, 1989, p. 71, Moscow, Izd. RiS), can be used, DT2803-60 of DATA TRANSLATION, in particular.

Block 7 of the illuminator control, following the computer system command, assigns the necessary level of the radiation intensity and spectral composition either for one common source of the optical radiation or for each of the separate sources and with the help of input-output controller 10 performs switching of one or another source or groups of the sources. The constructive principle of such systems is well known and is not the subject of this invention.

What is claimed is:

1. An apparatus for the investigation of distribution of physiological components in human body tissues over a preselected area of the body comprising:

illumination means for providing electromagnetic radiation to illuminate the preselected area of the body at one or more spectral bands;

control means operably connected to said illumination means for modulating said illumination means in both frequency and amplitude;

photodetector means for receiving and recording spatial distribution of intensity of electromagnetic radiation reflected from said preselected area of the body;

accumulator means operably connected to said control means and said photodetector means for:

forming sequences of video images over a preselected period of time from said recorded spatial distribution of intensity of said reflected electromagnetic radiation from said preselected area of the body;

subtracting a reference video image from any video image from said sequences of video images resulting in sequences of subtracted video images; and accumulating said sequences of subtracted video images for processing in a computer;

display means operably connected to said computer for displaying, based upon said sequences of subtracted video images, the distribution of physiological components in human body tissues over the preselected area of the body; and interface means for coordinating said control means with said photodetector means and said accumulator means by said computer.

2. The apparatus as defined in claim 1 wherein illumination means comprises a source of electromagnetic radiation and means for diffusing said electromagnetic radiation to provide uniform illumination to said preselected area of the body.

3. The apparatus as defined in claim 1 wherein the spectral band of said electromagnetic radiation is less than the frequency interval over which the frequency modulation is performed.

4. The apparatus as defined in claim 1 wherein said illuminator means comprises an array of electromagnetic radiation sources to provide nonuniform illumination to said preselected area of the body in order to provide points of illumination of said preselected area of the body.

5. The apparatus as defined in claim 4 further comprising optical means for varying the size, form and position of projection of said array of electromagnetic radiation sources onto said preselected area of the body.

6. The apparatus as defined in claim 4 further comprising:

another photodetector, in addition to said photodetector means, said other photodetector comprising an array of photodetectors arranged in a similar fashion to said array of electromagnetic radiation sources;

optical means interposed between said array of sources and said other photodetector for projecting an optical image of said array of sources on said preselected area of the body and focusing electromagnetic radiation from said optical image reflected from the preselected area of the body onto said other photodetector; and synchronous detector means operably connected to said other photodetector for synchronous recording of frequency and amplitude modulated electromagnetic radiation reflected at points shifted from said points of illumination of said preselected area of the body and for providing an output therefrom.

7. The apparatus as defined in claim 6 wherein said array of electromagnetic radiation sources and said array of photodetectors are combined into a single device wherein said sources and said photodetectors are arranged in alternating rows and columns.

8. The apparatus as defined in claim 6 wherein said array of electromagnetic radiation sources and said array of photodetectors are combined into a single device by arranging said sources and said photodetectors in alternating rows.

9. A method for investigation of distribution of physiological components in human body tissues comprising the steps of:

illuminating a preselected area of the human body to be investigated with electromagnetic radiation at one or more spectral bands;

recording spatial distribution of the intensity of reflected electromagnetic radiation from the preselected area of the human body continuously over a predetermined period of time;

forming sequences of video images from said recorded spatial distributions over said predetermined period of time;

subtracting a reference video image from any video image from said sequences of video images resulting in sequences of subtracted video images;

accumulating said sequences of subtracted video images for processing in a computer; and viewing, based upon said sequences of subtracted video images, the distribution of physiological components in human body tissues over the preselected area of the body.

10. The method as defined in claim 9 wherein said electromagnetic radiation provides uniform illumination to the preselected area of the body.

11. The method as defined in claim 9 further comprising the step of illuminating the area of the human body with an array of sources for nonuniform illumination of the points on the human body in patterns which vary in size, form and location.

12. The method as defined in claim 11 further comprising the step of using an array of photodetectors to record reflected radiation at points displaced from said points illuminated by said array of sources.

* * * * *